United States Patent
Kerschensteiner et al.

(10) Patent No.: US 10,299,898 B2
(45) Date of Patent: May 28, 2019

(54) METHOD FOR PREPARING A PARTIAL OR FULL DENTAL PROSTHESIS

(71) Applicant: VITA ZAHNFABRIK H. RAUTER GMBH & CO. KG, Bad Säckingen (DE)

(72) Inventors: Eva Kerschensteiner, Bad Säckingen (DE); Urban Christen, Bad Säckingen (DE)

(73) Assignee: Vita Zahnfabrik H. Rauter GmbH & Co. KG, Bad Sackingan (DE)

( * ) Notice: Subject to any disclaimer, the term of this patent is extended or adjusted under 35 U.S.C. 154(b) by 478 days.

(21) Appl. No.: 14/407,387

(22) PCT Filed: Jun. 13, 2013

(86) PCT No.: PCT/EP2013/062279
§ 371 (c)(1),
(2) Date: Dec. 11, 2014

(87) PCT Pub. No.: WO2013/186315
PCT Pub. Date: Dec. 19, 2013

(65) Prior Publication Data
US 2015/0132718 A1 May 14, 2015

Related U.S. Application Data

(60) Provisional application No. 61/660,266, filed on Jun. 15, 2012.

(30) Foreign Application Priority Data

Jun. 15, 2012 (EP) .................................. 12172219

(51) Int. Cl.
*A61C 13/00* (2006.01)
*A61C 13/01* (2006.01)
(Continued)

(52) U.S. Cl.
CPC .............. *A61C 13/01* (2013.01); *A61C 9/004* (2013.01); *A61C 9/0006* (2013.01);
(Continued)

(58) Field of Classification Search
CPC ................... A61C 13/00–13/225; G06F 17/50
See application file for complete search history.

(56) References Cited

U.S. PATENT DOCUMENTS

| | | | | |
|---|---|---|---|---|
| 4,583,947 A | * | 4/1986 | Hazar | .................... A61C 13/00 264/18 |
| 2004/0172150 A1 | * | 9/2004 | Perot | ...................... A61C 9/004 700/98 |

(Continued)

FOREIGN PATENT DOCUMENTS

| | | |
|---|---|---|
| CN | 102098980 A | 6/2011 |
| EP | 1 444 965 A2 | 8/2005 |

(Continued)

OTHER PUBLICATIONS

Chinese First Office Action with translation from corresponding CN Application No. 201380031396.X, dated Oct. 10, 2015, 11 pages.

*Primary Examiner* — Yogesh P Patel
(74) *Attorney, Agent, or Firm* — Christensen, Fonder, Dardi & Herbert PLLC; Curtis Herbert

(57) ABSTRACT

A method for preparing a partial or full dental prosthesis comprising
1.1. acquiring a patient's oral situation by taking an impression or by digital recording;
1.2. if required, digitizing the patient's oral situation;
1.3. selecting the teeth forming the dental prosthesis from a library of teeth or groups of teeth to obtain a virtual set-up of the teeth, which is positioned virtually in a space that takes the acquired patient's situation into account;
1.3.1 said library contains designs of dental arches, tooth shapes, tooth sizes (Continued)

1.3.2 said library contains designs of the gingiva, and
1.3.3 said library contains total set-ups and/or modular set-ups for all of Angle's bite classes;
1.4. if required, modifying the set-up obtained from the library;
1.5. virtually embedding the teeth arranged in the virtual set-up in a virtual gingiva;
1.6 producing the real prosthesis.

8 Claims, 9 Drawing Sheets

(51) Int. Cl.
*A61C 13/08* (2006.01)
*A61C 9/00* (2006.01)
*G16H 20/40* (2018.01)
*B33Y 10/00* (2015.01)

(52) U.S. Cl.
CPC ...... *A61C 13/0003* (2013.01); *A61C 13/0004* (2013.01); *A61C 13/0006* (2013.01); *A61C 13/0022* (2013.01); *A61C 13/082* (2013.01); *B33Y 10/00* (2014.12); *G16H 20/40* (2018.01)

(56) References Cited

U.S. PATENT DOCUMENTS

| | | | |
|---|---|---|---|
| 2008/0124676 A1* | 5/2008 | Marotta | A61C 1/084 433/174 |
| 2009/0034811 A1 | 2/2009 | Kuo | |
| 2013/0218532 A1* | 8/2013 | Thompson | A61C 13/0004 703/1 |

FOREIGN PATENT DOCUMENTS

| | | |
|---|---|---|
| EP | 1 459 702 A2 | 9/2005 |
| EP | 1 859 758 A1 | 11/2007 |
| EP | 1 864 627 A2 | 12/2007 |
| EP | 2 111 180 A1 | 10/2009 |
| WO | 2008005432 A2 | 1/2008 |
| WO | 2009017826 A1 | 2/2009 |
| WO | 2009026943 A1 | 3/2009 |
| WO | 2009105684 A1 | 8/2009 |
| WO | 2010105628 A2 | 9/2010 |
| WO | 2011066895 A1 | 6/2011 |
| WO | 2011077175 A1 | 6/2011 |
| WO | 2012055420 A1 | 5/2012 |
| WO | 2012061655 A2 | 5/2012 |

* cited by examiner

A    B    C    D

A

B

D

C

METHOD FOR PREPARING A PARTIAL OR FULL DENTAL PROSTHESIS

CROSS REFERENCE TO RELATED APPLICATIONS

This application is a national phase filing of PCT Application No. PCT/EP2013/062279 filed on Jun. 13, 2013, which claims priority to European Patent Application No. 12172219.3 filed Jun. 15, 2012 and U.S. Provisional Application No. 61/660,266 filed Jun. 15, 2012, both of which are hereby incorporated herein by reference.

TECHNICAL FIELD

The present invention relates to a method for preparing a partial or full dental prosthesis.

BACKGROUND

When patients are provided with partial or full dental prostheses, a high standard can be noted today. The dentist prepares the situation intended for restoration with the patient, while the (partial) dental prosthesis is usually prepared in an external laboratory or in the dentist's surgery by a dental technician according to the specifications obtained from the dentist. The quality of the prosthesis is highly dependent on the skills as a craftsman of the dental technician, who must take the specifications obtained from the dentist into account when preparing the prosthesis, and on the quality of such specifications.

INTRODUCTION AND SUMMARY

Further, the preparation of the patient to be provided with a prosthesis often causes inconvenience to the patient. For example, in this connection, there may be mentioned various sessions on the dentist's chair, in which impressions of the situation to be restored must be taken, which serve as negative replicas for the dental technician. The subsequent further impression-taking sessions are time-consuming, and are often the reason for an incorrect execution of the prosthetic restoration. Typically, two or three impression-taking sessions are required before the dental technician can begin with the actual production of the prosthesis.

WO 2011/066895 A1 relates to a method for the automated production of dentures, comprising the following steps: providing a digital data set of the individual prosthesis to be created; digitally separating the model into the dental arch and the gingiva; producing the dental arch from ceramic and plastic by means of milling technology; or producing the prosthesis base by generative or material-removal methods from predominantly (meth)acrylate-based plastics, connecting the dental arch and the gingiva by adhesive bonding or joining or a combination of adhesive bonding and joining.

EP 2 111 180 A1 relates to a method for producing a base part of a set of artificial teeth, or a set of artificial teeth having a base part, comprising the step of forming the base part by a rapid prototyping process, e.g. 3D lithography and, in particular, 3D laser lithography. Furthermore, the invention relates to a method of establishing a data set representing the shape of a base part of a set of artificial teeth, wherein a gum area or a model thereof is scanned and/or a model of a base part is scanned and/or the shape of the base part is simulated on a computer.

EP 1 864 627 A2 discloses a method for manufacturing dental prostheses according to a digitized virtual model which reflects the maxillary situation, comprising the steps of providing a data record that reflects the maxillary situation and relationship, digital tooth modeling (automatically as an option), creating a divided negative mold (rapid manufacturing) from the data from the digital tooth modeling, insertion of the fabricated teeth/tooth units into the opened negative molds, closing the negative molds, and filling the remaining cavities with plastic for prostheses.

EP 1 444 965 A2 relates to a method for manufacturing a dental prosthesis, comprising the steps of recording and digitizing (scanning) 3-dimensional, anatomical relationships in an oral cavity; optionally recording and digitizing (scanning) 3-dimensional data on bite rims including bite walls; optionally recording of mandibular data, which normally are taken on a patient for placement of an articulator; processing of data record obtained in such a way that relevant anatomical structures for virtual placement of teeth are established, and a virtual model is obtained as a data record; followed by selecting 3-D data records of fabricated, previously scanned teeth from another data record; virtual placement of the teeth into the virtual model as a second data record; and either followed by transferring the virtual placement to the model by either a positioning template (e.g., milled or rapid-prototyped), or direct placement of the fabricated teeth on the model; affixing the teeth to the model; attachment of a denture base; or in another alternative, followed by direct manufacture of the denture base, according to the data for a virtual denture placement, with positioning aids for the final correct positioning and affixing of the fabricated teeth.

WO 2008/005432 A2 discloses a system for fabricating at least a portion of a denture. The system includes a three-dimensional scanning device for scanning a surface of a denture template, and a computer-readable medium including a computer program for receiving data from the scanning device, creating a 3-dimensional model of the surface, and optionally modifying the 3-dimensional model and/or adding features to the 3-dimensional model. The system also includes a processing unit for creating at least a portion of the denture, from a selected material, based on the 3-dimensional model. The processing may be material-removing or additive in nature.

WO 2012/055420 A1 discloses a method for detecting a movable object in a location, when scanning a rigid object in the location by means of a 3D scanner for generating a virtual 3D model of the rigid object, wherein the method comprises: providing a first 3D representation of at least part of a surface by scanning at least part of the location; providing a second 3D representation of at least part of the surface by scanning at least part of the location; determining for the first 3D representation a first excluded volume in space where no surface can be present; determining for the second 3D representation a second excluded volume in space where no surface can be present; if a portion of the surface in the first 3D representation is located in space in the second excluded volume, the portion of the surface in the first 3D representation is disregarded in the generation of the virtual 3D model, and/or if a portion of the surface in the second 3D representation is located in space in the first excluded volume, the portion of the surface in the second 3D representation is disregarded in the generation of the virtual 3D model.

WO 2010/105628 A2 discloses a method for planning, visualizing, and/or optimizing dental restoration on at least a part of the pre-prepared teeth of a patient, wherein said method comprises the steps of:—providing at least one 3D digital model of at least a part of the pre-prepared teeth;—designing at least one dental restoration CAD model based on the 3D digital model of at least a part of the pre-prepared teeth;—providing at least one 3D digital model of at least a part of the prepared teeth, where the prepared teeth are provided by preparing the pre-prepared teeth by dental restorative work, at least partly based on the dental restoration CAD model; and—aligning the 3D models of the pre-prepared and the prepared teeth.

WO 2012/061655 A2 discloses a system and processes for optimal selection of teeth for dentures based on the anatomical measurements and bite impressions of the patient. This information is applied in an iterative manner to rules that balance the anatomical and aesthetic considerations to select the best teeth for a patient. The system may also use this information in an iterative manner to rules that balance the anatomical and aesthetic considerations to design the optimal denture base for the patient as well.

US 2009/0034811 A1 discloses embodiments which are provided for accurately characterizing a tooth's movement. One method embodiment includes associating an abnormal tooth shape with a model tooth shape from a reference library of model tooth shapes, mapping a predefined dental reference from the model tooth shape onto at least a portion of the abnormal tooth shape, and adding a location of the predefined dental reference to the abnormal tooth shape based on the mapped predefined dental reference from the model tooth shape.

WO 2009/017826 A1 discloses dental appliances, devices, and methods of making and using such appliances. In one embodiment, a method for tooth modeling includes receiving a patient information file for a treatment plan patient and analyzing the patient information file to determine whether the patient is a non-adult patient.

EP 1 859 758 A1 discloses a block made of ceramic compounds, in particular dental compounds, of at least one ceramic compound with predetermined first optical properties and at least a second ceramic compound with predetermined second optical properties, and of a transition area between the two ceramic compounds, which transition area is composed of changing mixtures of the at least two ceramic compounds, the variation gradient of the mixtures being substantially constant.

WO 2011/077175 A1 discloses a method to create removable dental prosthesis, and the dental prosthesis making thereof, which is suitable for quick and efficient production of removable dental prostheses. During the method according to the invention a digital data recording is made of the oral cavity without teeth, or with partial teeth-deficiency, or of the model taken of it, then the information received this way is processed by a computer with the help of a targeted software, and the virtual digital image of the removable tooth replacement (prosthesis) is created, and on basis of the virtual digital image of the prosthesis the finished product of the prosthesis itself, the base plate and the teeth are made with the help of a prototype making equipment of unique model-building. Characteristic of one method according to the invention is that the prosthesis is produced from the established digital model with a spatial 3D printer (PRI) suitable for printing several different colors, several different raw materials from a thermoplastic raw material with a method based on melt layering, preferably with a Fused Deposition Modeling, (FDM) method. Characteristic of one method according to the invention is that the prosthesis is produced from the established digital model with a spatial 3D printer (PRI) suitable for printing several different colors, several different raw materials from a biologically compatible liquid composite plastic material setting under laser or UV light, preferably with Multi Jet Modeling (MJM) method. Further the invention is dental prosthesis, which is primarily made using the method according to the invention, preferably with melting (FDM) process using bearing material and raw materials of several colors applied layer by layer within a production process.

WO 2009/026943 A1 discloses a method to produce a dental prosthesis, with the steps: mechanical and/or optical scanning of a mucous membrane structure in a toothless area of a lower jaw or upper jaw in order to determine a data record describing the three-dimensional shape of the mucous membrane structure; determination of a data record describing the three-dimensional shape of a removable dental prosthesis, wherein the three-dimensional shape of the dental prosthesis has a mucous membrane area, complementing the three-dimensional shape of the mucous membrane structure, and an adjoining tooth area; and control of a machine, using the data record describing the three-dimensional shape of the dental prosthesis, in order to machine the three-dimensional shape of the dental prosthesis from a plastic preform which has an area with a first colour and an adjoining area with a second colour, wherein the mucous membrane area of the three-dimensional shape of the dental prosthesis is formed in that area of the plastic preform with the first colour, and the tooth area thereof is formed in that area of the plastic preform with the second colour.

The object of the present invention is to provide a method that enables a simple and reliable production of a full prosthesis or partial prosthesis.

This object is achieved by a method according to claim 1. The claims depending on claim 1 relate to reasonable further embodiments of the method according to the invention.

Further independent claims relate to a method for reliably assigning the tooth oriented in a set-up to the denture base, to a library containing data relating to tooth set-ups and gingival designs, to a tooth comprising an assigning element and a denture base material comprising an assigning element, as well as to a defined set-up of teeth for preparing a prosthesis.

In detail, the method according to the invention for preparing a partial or full dental prosthesis includes the following steps:

1.1. acquiring a patient's oral situation by taking an impression or by digital recording;
1.2. if required, digitizing the patient's oral situation;
1.3. selecting the teeth forming the dental prosthesis from a library of teeth or groups of teeth to obtain a virtual set-up of the teeth, which is positioned virtually in a space that takes the acquired patient's situation into account;
   1.3.1 said library contains designs of dental arches, tooth shapes, tooth sizes
   1.3.2 said library contains designs of the gingiva, and
   1.3.3 said library contains total set-ups and/or modular set-ups for all of Angle's bite classes;
1.4. if required, modifying the set-up obtained from the library;
1.5. virtually embedding the teeth arranged in the virtual set-up in a virtual gingiva;
1.6. producing the real prosthesis.

"Partial or full prosthesis" means a denture that is removable, conditionally removable, or permanently attached.

The taking of an impression of the situation of the patient's mouth (patient's situation) can be effected, in particular, by using impression materials. According to the invention, the impression can be advantageously used as a putty impression, second impression (functional impression), and bite registration.

In the method according to the invention, the impression can be taken with conventional devices, so-called impression trays. An impression tray that enables a mucosa-congruent seat is particularly suitable. The border regions are to be reduced. The impression tray is to be capable of receiving impression material, and of receiving a vertical mechanism for bite adjustment, and susceptible to posterior geometries for bite fixation.

In one embodiment of the present invention, the digital recording of the patient's situation is performed by means of imaging, especially optical, methods, such as camera recording, computer tomography, ultrasound.

In another embodiment of the method according to the invention, the library contains representations of dental arches, dental shapes, dental sizes, dental shapes/sizes and combinations thereof, as can be seen, for example, from VITAPAN® or VITAPAN® plus mould charts Nos. 1694 and 1756. Total set-ups and/or modular set-ups for all Angle's bite classes are preferably considered in the library. If desired, the library may also contain designs of the gingiva in different age manifestations.

The method according to the invention advantageously enables the dental arch to be adapted to the individual span and curve of the patient's jaw by considering virtual hinges that are widened by a function in the form of a motion element (inward and outward motions), for example, between teeth 11 and 21 in the upper jaw and teeth 31 and 41 in the lower jaw. The design of the gingiva can be individualized virtually, for example, by inserting palatine folds or adapting the vibrating line (Ah line) and the scrapings. For the palatine folds, deposited virtual models of the folds are preferably inserted into the virtual model of the prosthesis.

It may be convenient to change the models individually in accordance with the denture shape, for example, by stretching and compressing and by mapping onto the palatal surface. The scraping is modified by virtual changes of the material thickness near the Ah line, and the Ah line itself (FIG. 5) can be indicated as a curve or bordering line and changed in the virtual model.

In another embodiment of the method according to the invention, the production of the real prosthesis is effected by
a. preparing a prosthesis base;
b. providing a tooth receiving means; and
c. inserting prefabricated teeth, followed by
d. completing the total prosthesis.

In this embodiment, the production of the total prosthesis may also be effected by an additive fabrication method. The prosthesis base can be prepared by additive fabrication or abrasive fabrication.

The present invention also discloses a library containing data relating to tooth set-ups and gingival designs for preparing a partial or full dental prosthesis.

The present invention further relates to a method for reliably assigning a tooth oriented in a set-up to the denture base using complementary assigning elements on the tooth and denture base, or using a per se known template technique. Thus, the tooth positions can be fixed and transferred to the prosthesis.

The method according to the invention and its embodiments, and also, in particular, the further subject matters of the invention, enable a defined set-up of teeth for producing a prosthesis, especially obtainable from the library disclosed herein, to obtain a virtual set-up of the teeth that is virtually positioned in a space formed by recording the patient's situation.

DETAILED DESCRIPTION

Figure 1:
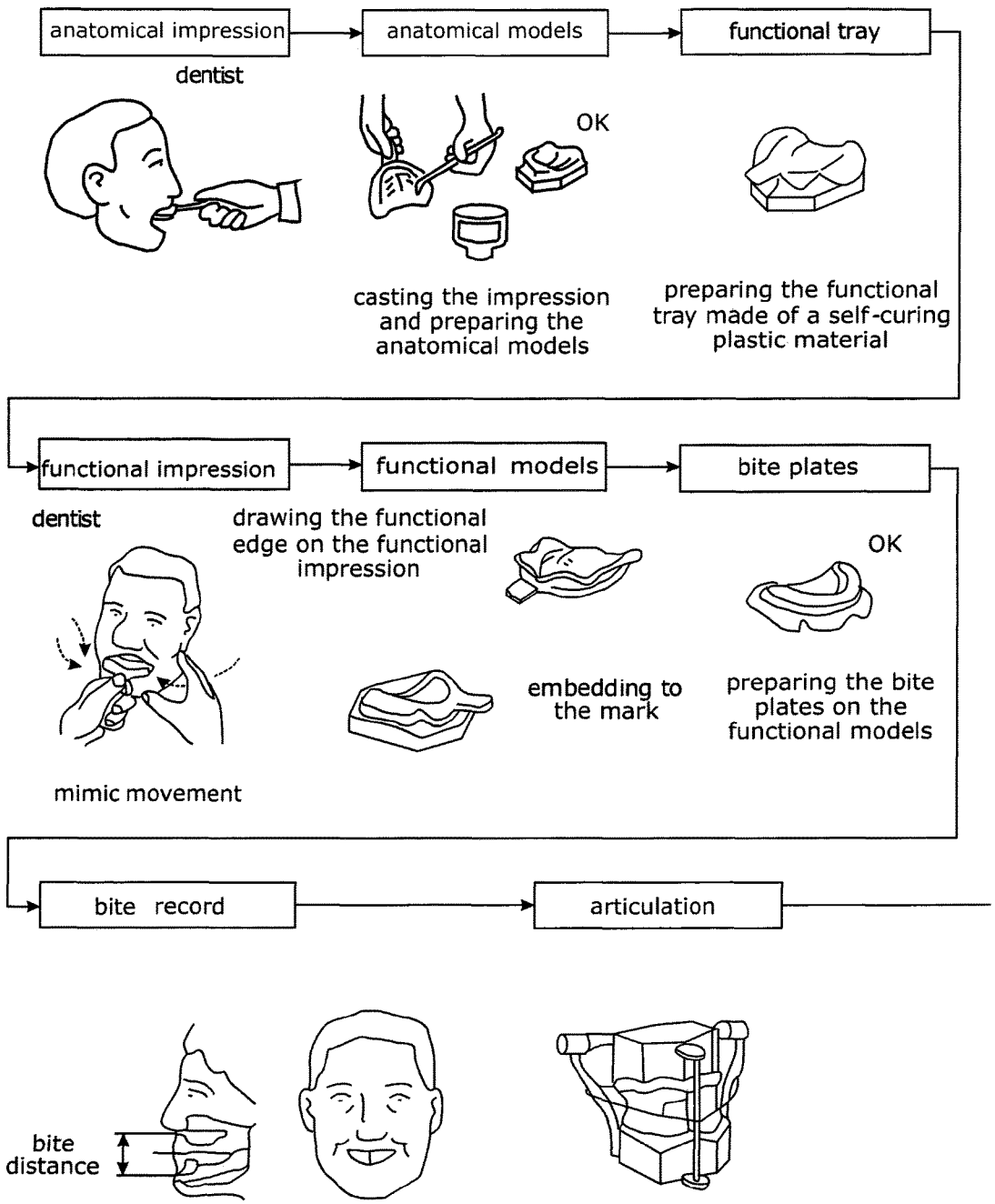
FIG. 1: The Figure shows the recording of a patient's situation (putty impression, functional impression, bite registration).

By the method according to the invention, the recording of patient information (putty impression, functional impression, bite registration) is effected, for example, by
a) conventional impression;
b) using an impression tray meeting the following criteria: mucosa-congruent seat, reduced border regions, capable of receiving impression material, and of receiving a vertical mechanism for bite adjustment, and susceptible to posterior geometries for bite fixation.
c) by optical recordal digitizing by means of suitable sensors
  1. by digital recording
  2. by computer tomography
  3. by optical methods.

The analogous data obtained by taking impressions are converted to digital data. This may be effected by optical recordal digitizing as stated under c).

In the method according to the invention, the recording of the patient's situation is preferably performed in one session as putty impression, functional impression, and bite registration.

In conventional impression, the following procedures can be employed (Lehrbuch der Zahntechnik, Volume 1, A. Hohmann/W. Hielscher, Quintessenzverlag; Die totale Prothese, Peter Lerch, Quintessenzverlag; Die Logik in der Totalprothese, Quintessenzverlag; Die Totalprothese, Grundler/Stuttgen, Verlag Neuer Merkur).

For example, the dentist takes an anatomical impression with prefabricated trays or standard production trays. An impression tray that can acquire the functional impression, centricity and vertical dimension in one session is suitable, in particular. Subsequently, the production of the anatomical models can be performed by the dental technician by casting the impressions with plaster, for example, in a dental technology laboratory. Thus, the method according to the invention includes the following steps.
1. Preparing the functional trays (individual tray).
2. Taking functional impressions with the functional trays (individual trays).
3. Preparing the functional edge models by casting the functional impressions with plaster.
4. Preparing the bite plates.
5. Maxillomandibular relationship record (determining and fixing the spatial position of the lower jaw relative to the upper jaw) by means of the bite plates.

These steps can be performed by suitable personnel depending on their education and legal conditions, for example, by dentists or dental technicians.

Item 1.: Individual Functional/Impression Tray:

The taking of the impression with an individual tray serves for specification of the putty impression with prefabricated trays. It should be taken care that a functionally correct extension and a regular layer thickness of the impression material are enabled in the taking of the second impression. The individual impression tray should cover mucosa only if it offers a bony substrate. The aim of the functional impression is to maximize the seating surface of the prosthesis body with consideration of the muscular movements. In order to get the total prosthesis to grip on the edentulous jaw, a suction effect is to be achieved between the base and mucosal surface. The latter is achieved by the cohesion and adhesion forces of a precisely fitting prosthesis. In order to retain the suction effect also during the speaking and chewing functions, it is required to shape the functional edges, i.e., the inner and outer valve edges. Before the impression is taken, the future prosthesis seat should be in a recovered state, i.e., the old prosthesis has not been worn recently, in particular, for at least 24 hours.

The functional impression is taken by means of individual functional trays prepared by the dental technician on the first working models, the anatomical models.

Before they are prepared, information relating to the properties of the impression material with which the functional impression is to be taken is required in order to:
prepare precisely fitting trays for low viscosity material;
design trays leaving a uniform space from the model for high viscosity material.

The tray material should be sufficiently hard and free of torsion.

Dimensions of the Functional Tray:

The dimensions of the tray should be smaller than the area to be covered of the future denture seat, and the portions around the labial frenulum and buccal frenums as well as around the lingual frenulum should be generously left free.

It is recommendable to design the edges of the individual tray slightly shorter than the later denture edge on the vestibular side. In particular, in the region of the Ah line, the tray is overextended by about 2 mm as compared to the later dorsal denture edge. The edge region of the individual trays is designed in a thickness of about 2 mm as known to the skilled person.

Preferably, the labial frenulum and buccal frenums are exposed in such a way as not to be compressed or squeezed during the taking of the impression. For example, in the second impression, the attending person completes the tray edges by a thermoplastic (reversibly rigid) impression material. Thus, the sought suction effect can be achieved by insulation in the edge region.

In this way, the design of the inner and outer valve edges can be prepared as functionally appropriate as possible in the mouth. The edges should be spared from the model preparation to the readily polished prosthesis, so that this valve effect is not cancelled.

Item 2.: Functional Impressions Taken With the Functional Trays:

In the taking of impressions of the edentulous jaw that take the muscles adjacent to the denture seat into account, mucostatic and mucodynamic methods are distinguished. In mucostatic methods, there is confidence that the respective impression material enables the functionally appropriate taking of an impression even without active muscular movements by the patient because of the existing muscular tension, the so-called muscle tone at rest. In the mucodynamic methods, the patient exerts all kinds of muscular movements in contrast to the mucostatic impression technique, in order to actively shape the impression material bulging out over the edge of the tray by the moving muscle strokes and thus ultimately to exclude overextension of the later denture edges. Depending on the patient's situation, different impression methods are applied for the upper and lower jaws.

The functional impression is supposed to represent:
in the upper jaw:
the vestibular fold
the alveolar ridge with the regions of maxillary tuberosity and palate
transition from the hard to the soft palate (Ah line)
labial frenulum and buccal frenums
in the lower jaw:
the alveolar ridge with the regions of trigonum retromolare (retromolar triangle)
the vestibular fold and sublingual regions
muscle and frenum insertions of the lingual and buccal muscles
labial frenulum and buccal frenums Item 3.: Preparation of the Functional Edge Models by Casting the Functional Impressions:

A hard plaster of class IV can be used for preparing the models. In highly undercut alveolar ridges, a hard plaster of class III may also be used. It should be taken care that the functional edges are preserved as completely as possible. The skilled person knows the measures necessary for this purpose, for example, attaching a strip of functional edge protection wax/crash barrier wax by means of adhesive wax.

When the functional models are prepared, it should be taken care that the functional edges are preserved as completely as possible. For the functional edges form the later valve edges, which enable a suction effect between the prosthesis base and the mucosa.

Item 4.: Preparing the Bite Plates:

So-called bite plates are required in order that the attending person may "lock" or fix the upper and lower jaws in their mutual relationship. These consist, for example, of a plastic material in the base with a bite rim of wax. The latter should be hard. The base may also be prepared from a wax plate.

When the edges are designed, care should be taken that these are not sharp-edged or too long. The wax bite rim is usually placed in the course of the middle of the alveolar ridge. The chewing plane is virtually parallel to the alveolar ridge contour of the upper jaw. In the lower jaw, the course is limited by the upper thirds of the retromolar triangles. In the region of the front (in the upper and lower jaws), the attending person can build the bite rims partially with wax in order to achieve a lip volume/support appropriate to the case.

The height of the individual bite rims as measured from the vestibular fold is shortened to such an extent that values of from 20 to 22 mm are obtained in the upper jaw, and values of from 18 to 20 mm are obtained in the lower jaw. Studies have shown that these values are at the upper limit. Items to be observed in the production are listed in the following:

- For a maximum of freedom for the tongue, the anterior regions of the wax walls are given a thin design.
- The design of the edges of the bite plates should be made considering the functional edges. Frenums and muscle insertions must be exposed.
- With respect to the labial and buccal dimension, the wax walls should correspond to the later prosthesis. The width of the wax walls should be about 6 mm in the premolar region and about 8 mm in the molar region.
- The wax walls should be in the middle of the alveolar ridge. Exception: In the maxillary anterior region, the wax wall is oriented according to aesthetic aspects (extended to the fore) and should support the lip according to the set-up of the anterior teeth.
- The "incisal edge" in the upper jaw should be about 7 mm from the papilla incisiva as a starting value.
- The height of the wax wall in the upper jaw is about 20 to 22 mm as measured from the vestibular fold (in the region of the labial frenulum) to the upper edge of the bite rim.
- The height of the wax wall in the lower jaw is about 18 mm as measured from the vestibular fold (in the region to the side of the labial frenulum) to the upper edge of the bite rim. The distal height in the upper and lower jaws is achieved by melting down the bite rim with a rim former.
- The distal height should correspond to the upper third of the trigonum retromolare.
- The wax walls of the upper and lower jaws should fit neatly against each other.
- The total height of the bite plates should be not more than 40 mm.

The final shaping of the wax walls is usually performed by the attending person on the patient.

They orient the occlusal plane by the bipupillar line and by Camper's plane using a bite fork. In addition, they will build up the buccal region with wax until an optimum cheek contact has been achieved. Such guide points must be secured and fixed accordingly in the laboratory. This can be done, for example, with a silicone or plaster index (also referred to as a "pattern"). With this index, it can be subsequently checked permanently during the set-up whether the cheek contact according to the wax bite is ensured.

Item 5.: Maxillomandibular Relationship Record:

The maxillomandibular relationship record relates to measures by which the spatial position of the edentulous lower jaw relative to the upper jaw is determined and fixed. The following marks to be made by the attending person are indispensable:

- Determination of the center line, center of the face
  - It need not be identical with the upper and lower labial frenulums or the center of the model.
- Determination of the cuspid line
  - It is critical to the width of the upper anterior teeth. It is to define the positions of the tips of the upper canine teeth. It can be determined through the corners of the mouth or through a vertical extension of the outer wings (alas) of the nose.
- Determination of the smile line
  - It is critical to the length of the upper anterior teeth. The tooth necks should normally ne above this line.
- Determination of the occlusal plane
  - It runs over the upper edge of the lower wax wall (=lower incisal edges in the anterior tooth region, and tips of the distobuccal cusps of the second lower molars) and forms a point of intersection with the center line, which is the fixing point for the incisal index. It runs parallel to Camper's plane.

In order to prepare as flawless as possible a prosthetic restoration, a putty impression is taken in the patient's mouth according to the invention using a prefabricated standard tray (disposable or not) and an alginate impression material. Finally, these impressions are cast with modeling plaster. From these models, an individual (patient-based) impression tray is prepared later. With this latter tray, an impression of the mouth situation is taken mucodynamically (i.e., under all movement influences of the muscles and ligaments). Cast with modeling plaster, this second model forms the working base for dental prostheses.

A suitable impression tray is based on a family of prefabricated impression trays, with edge regions having a short design following the example of J. Schreinemakers. However, these are not provided with retention holes and additionally include a means for adjusting the vertical dimension in the upper jaw and an oral plate seat of the anterior tooth region in the lower jaw, rather than a handle, which is often irritating for the patient's maxillomandibular relationship record. Further, the upper as well as lower jaw trays include geometric shapes in the posterior region to enable a flawless repositioning in the maxillomandibular relationship record, for example, by means of bite silicone. In addition, the labial region includes a lip support, preferably made of the same material as the tray. It serves to check the lip volume and can be reduced by milling, or modified according to the patient using a bit of wax, if necessary.

1. In detail, the correct tray size can be selected from the range my means of a measuring loop. This holds for both the upper and the lower jaw.
2. Using a thermoplastic (reversibly rigid) impression material (e.g., GC Bite Compound), which is either industrially prefabricated or individually applied, primarily three stops made of the thermoplastic (reversibly rigid) material are set for positioning the upper jaw tray and positioned in the patient's mouth. Disturbing regions are eliminated. Now, the edge impression material is brought into a shapeable consistency by heating, for example, in a water bath. Thereafter, the tray is inserted into the patient's mouth, and an impression of the edge regions is taken mucodynamically. If necessary, further correction material can be applied. If a suction effect was achieved through the edge region, a fine impression with low viscosity silicone can be performed. After the impression is completed, excess material (e.g., dorsal appendices) is eliminated.

3. For taking an impression of the lower jaw, exactly the same method is used as in the preceding paragraph.
4. For determining the vertical dimension and the speaking distance, the device is corrected upwards or downwards in the anterior region of the upper jaw in accordance with the phonetic results (determined by speaking checks). Thus, the dimension in the vertical direction can be secured for the attending person.
5. The maxillomandibular relationship record is not determined with drawing a gothic arch as with other conventional systems, but is done with the assistance of the patient's tongue. Thus, a tongue orientation (small geometric shape, e.g., a sphere, pyramid or the like) is employed. The latter is attached, for example, at the dorsal prosthetic edge of the upper jaw using an adhesive material, such as wax. The upper jaw impression and the lower jaw impression are now introduced into the patient's mouth. The patient may move freely in the horizontal plane. He may be instructed by the attending person to run with the tongue along the palate towards dorsal and to touch the tongue orientation with the tip of the tongue. Meanwhile, the attending person adds some impression material, such as bite silicone, to the left as well as the right posterior regions and, in particular, they inject the impression material through a cannula in order to lock the two jaws together. The geometries in the lower jaw are slightly undercut, which enables, in particular, retentive anchoring of the impression material, such as bite silicone. After both the centric and the vertical relationship have been fixed, excess impression material can be removed. This enables the determination of centricity to be checked. If a change must be made, the bite silicone can be easily removed, and the record is repeated if necessary. The vertical dimension is secured and need not be repeated, because the silicone fixations can be positioned repeatedly.

a) Optical recordal digitizing by means of suitable sensors

A direct preparation of digital models of the oral cavity without taking impressions can significantly simplify and accelerate the whole process chain for the attending person, and increase the exactness of the information obtained. This makes the treatment substantially more comfortable for the patient. For this reason, great efforts are currently made to make corresponding systems marketable. However, problems existing in all approaches currently include:

the simultaneous acquisition of teeth and gingiva
the precise acquisition of the flexible mucosa.

In principle, the methods for digitizing the geometrical shape of bodies can be classified into two classes:

surface-oriented methods; and
volume-oriented methods.

By means of surface-oriented methods, the coordinates of points on the surface of an object are acquired. This can be done, for example, with tactile touch probes (e.g., Renishaw company), but for intraoral applications, contactless sensors are preferably employed. With contactless sensors, the coordinates of the surface points can be determined by measuring the distance of the surface from the sensor element. This can be done by either measuring times of flight or by optical triangulation.

Known time of flight measuring methods are based on the use of ultrasound waves, terahertz radiation, microwaves, but also visible light, for example, in optical 3D cameras ("time of flight"), in which the times of flight of the light are typically made measurable by means of frequency modulation and determining the phase shift. In particular, methods that sense the surface not only point by point (such as ultrasonic sensors and microwave sensors), but represent a partial area of the surface in a record are of interest for the practical application. The latter recording methods include optical time of flight measuring methods as well as terahertz methods. However, these are currently less suitable for the digitization of dental topographies because of insufficient exactness according to the current state of the art. Terahertz waves are strongly absorbed even by a thin film of liquid as an aggravating factor.

In triangulation measuring methods, patterns projected onto the surface of the object are recorded in a known geometric arrangement of projectors and receivers, and their shift and/or deformation is evaluated by means of the trigonometric relationships in the arrangement.

In addition to conventional white lamps, lasers are also employed as light sources for the projection of individual points or individual lines. However, the projection of the usually employed striped patterns is effected exclusively with white light sources. The complexity of the surfaces to be acquired has the effect that the patterns on the surface are recorded simultaneously with several detectors, typically video cameras, from different perspectives. Such arrangements also enable self-calibration of the measuring system. Corresponding devices are available on the market, enabling the contactless digitization of teeth as well as of non-flexible gingiva. For preparing a sufficient contrast for the optical acquisition of the patterns, it is necessary with many devices to pretreat the surface with white powder spray.

Volume-oriented methods are based on the transmission of radiation through the object to be measured, and the calculation of the local material-specific absorption of radiation. Thus, the object is placed between the radiation source and a suitable detector arrangement, and radiographic images of the object are recorded at different angles, from which the (material-specific) absorption values in the radiographed volume are then calculated in a mathematical process. In the dental industry, X-ray computer tomography (CT) is a frequently employed method. A distinction is to be made between classical tomography and digital volume tomography (cone beam tomography, DVT). In classical CT, radiation is transmitted respectively through a thin layer of the object, and a volume is produced by stacking many layer images. In this process, a linear arrangement of radiation-sensitive detectors is employed, and the detector/source system is displaced relative to the object along the rotation axis to record several layers of the object. In volume tomography, the object is radiographed by conically propagating X-rays, and a two-dimensional array of X-ray-sensitive detectors ("X-ray camera") is used as a detector. Thus, the object can be acquired completely in one position without additional shifting. Although both methods are known in the dental industry, their use for digitizing the oral cavity is described here for the first time.

After the surface points have been measured by one of the methods described, a mesh of triangles is constructed from the points (STL format). This data structure enables efficient accessions to the data, the visualization of the surfaces with a wide variety of software products, and especially the generation of motion sequences of processing machines controlled by computerized numerical control (CNC) to prepare the surface described by the points.

The conversion to digital data of the impressions prepared analogously according to the above description can be effected, in particular, according to the following flow chart.
1. Conditioning (dusting with scanning powder) of the impressions and the bite record.
2. Fixation of the objects to be measured by means of a specific support on the positioning unit.
3. Start of the automatic measurements for digitizing the impressions, for example, with striped light, etc. Depending on the measuring method employed, the objects are acquired from several perspectives, and the thus obtained partial views are composed to a virtual overall view. To scan a complete jaw model, it is measured by means of four movement axes in partial segments under different perspectives, which are set by means of a positioning unit.
4. The individual measurements are subsequently composed by the software to give a complete data set.
5. The scanner yields a three-dimensional image of the model.
6. The results are available in STL data format and can be used for computer-aided design and for the automated fabrication of dental restorations.
7. Processing the data.

This procedure enables for the first time the provision of basic data and enables the virtual set-up and positioning of the shapes of prosthetic teeth deposited in a data base.

After basic data for the prosthetic restoration of a patient have been determined according to the working method described above, the set-up and positioning can be effected virtually on a computer and in a way individually adapted to the patient's situation.

Figure 2:
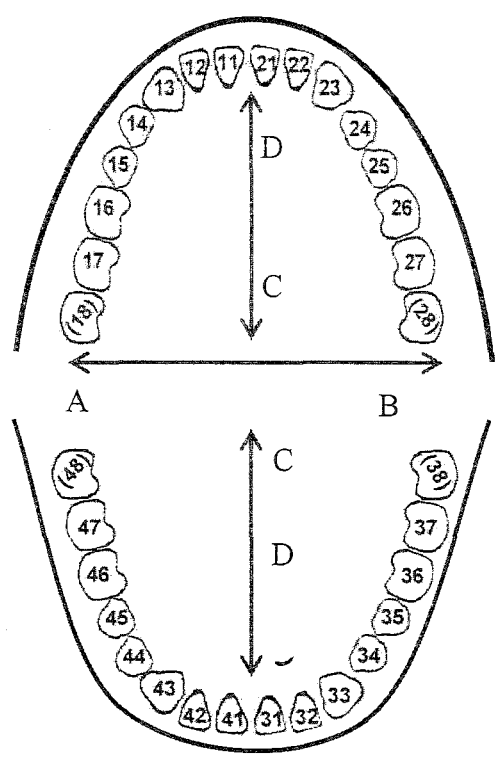
FIG. 2: The Figure shows the set-up and positioning of the teeth in the upper (A) and lower (B) jaws.
Figure 3:
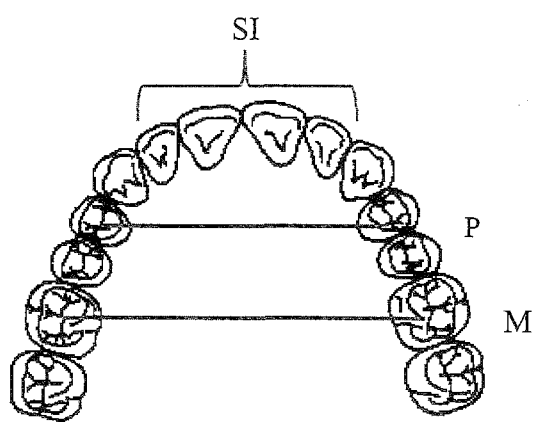
FIG. 3: The Figure shows an average ratio between the width of all four incisors in the upper jaw.

FIGS. 2 and 3 basically describe how the set-up and positioning of the teeth can be effected in the process according to the invention, observing the following points, for example:
1. Selection of rows of teeth according to the generally acknowledged average morphology of the rows of teeth as described, for example, in the "Lexikon der Zahntechnik" by Hohman/Hielscher.
2. a) defining the reference lines on the edentulous upper jaw;
   b) defining the reference lines on the edentulous lower jaw;
3. Maxillary anterior tooth modules
   a) observing the standards for the position
   b) observing the standards for the orientation
4. Mandibular anterior tooth modules
   a) observing the standards for the position
   b) observing the standards for the orientation
5. Set-up of posterior teeth
   a) set-up of mandibular posterior teeth
   b) set-up of maxillary posterior teeth
6. Assignment according to Angle's bite classification
   a) class I
   b) classes II/1 and II/2
   c) class III
7. Assignment according to bite types
   a) normal bite
   b) end-to-end bite
   c) cross bite
   d) scissor bite The above list in note form is explained further in the following.

1. According to the invention, the set-up and positioning of the teeth is effected according to a generally valid average morphology of the rows of teeth (FIG. 2).

For example, the upper dental arch is arranged in the form of half an ellipse. The axis A-B is about 55-62 mm, and the axis C-D is about 50-55 mm.

The lower dental arch typically follows the course of a parabola. The axis A-B is about 55-60 mm. The axis C-D is about 48-52 mm.

The dental arch width is obtained from the average ratio between the width of all four incisors in the upper jaw (sum of all 4 incisors=SI) and the width of the dental arch in two sites, namely from the transversal distance between the first premolar and the first molars (FIG. 3).

Figure 4:
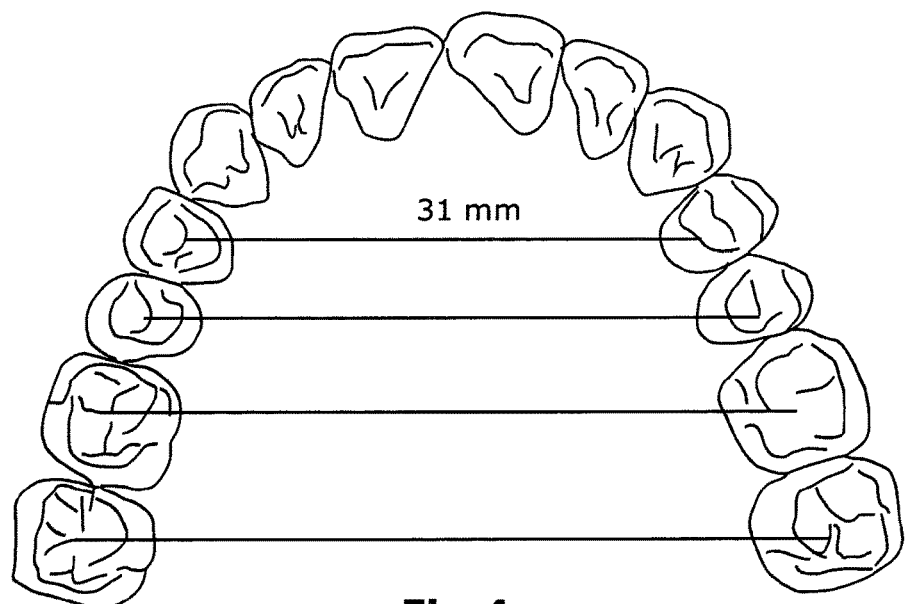
FIG. 4: The Figure shows average transversal distances between posterior teeth.

Average transversal posterior tooth distances. In the set-up of a total prosthesis, these serve as an orientation aid and as a possible check, because the posterior teeth should always adopt approximately their former positions (FIG. 4).

Figure 5:
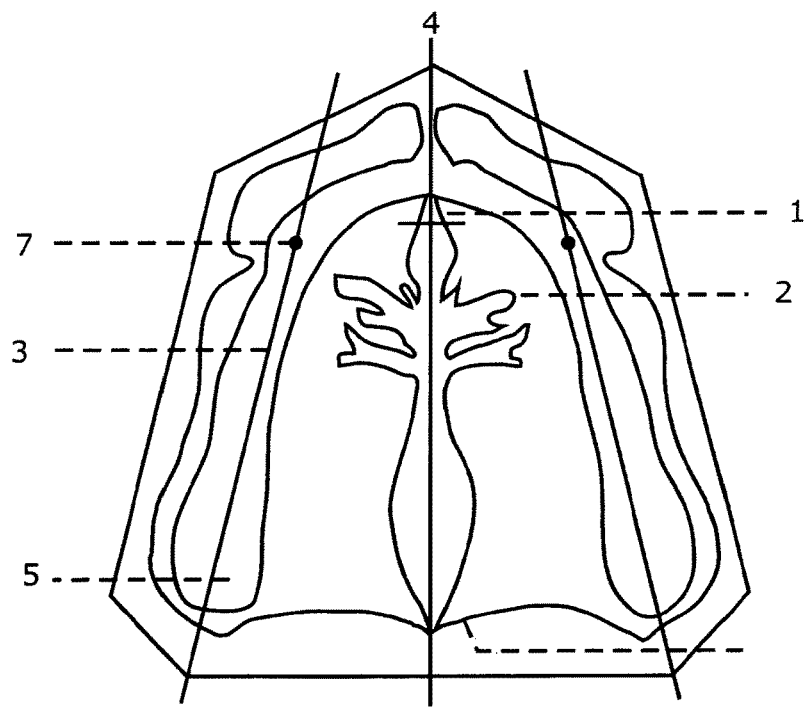
FIG. 5: The Figure shows reference lines on an edentulous jaw.
Figure 6:
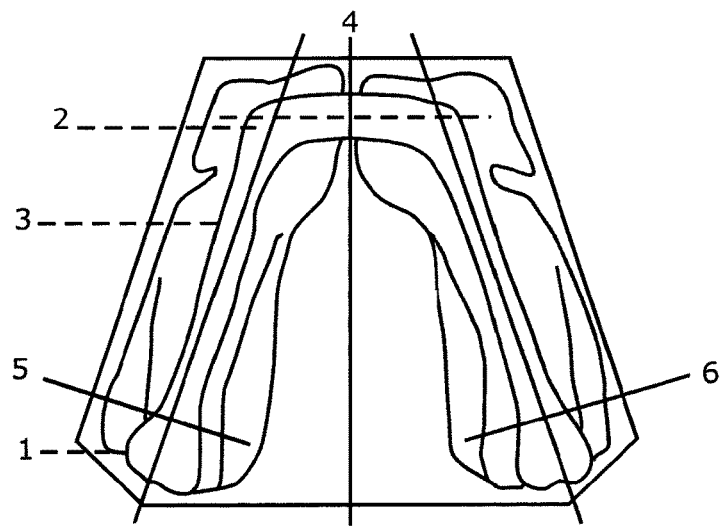
FIG. 6: The Figure shows reference lines on an edentulous lower jaw.
Figure 7:
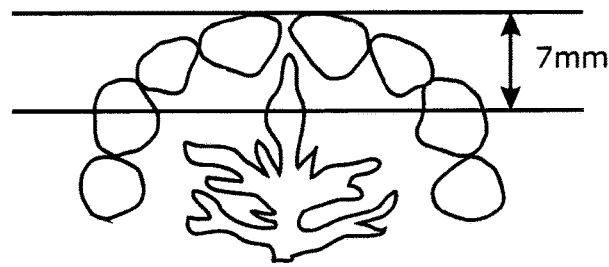
FIG. 7: The Figure shows anterior tooth modules for the upper jaw.
Figure 8:
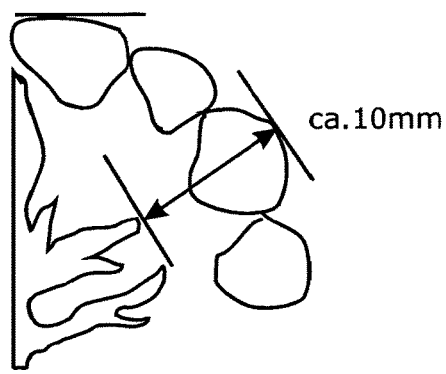
FIG. 8: The Figure shows standard rules for the positions of maxillary anterior teeth.
Figure 9:
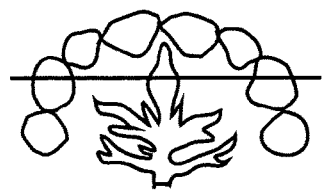
FIG. 9: The Figure shows the connecting line between the two tips of the canine teeth in the upper jaw (CPC line).
Figure 10:
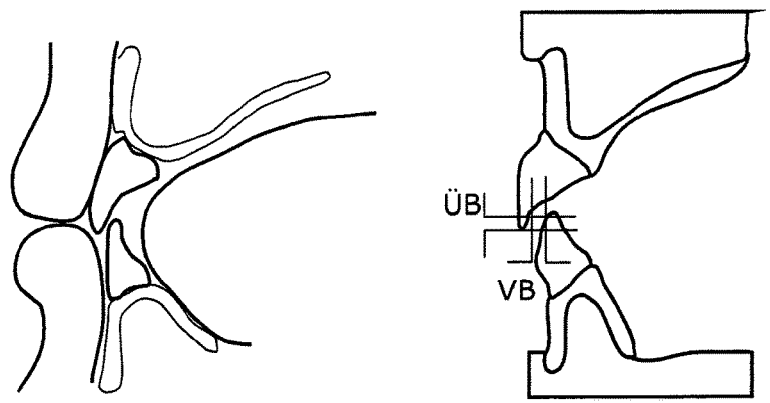
FIG. 10: The Figure shows the labial surfaces of the upper anterior teeth.

2. Reference lines on an edentulous jaw. The reference lines serve for orientation on an edentulous jaw and thus for the reproduction of the natural chewing function by means of dental prostheses.
   a) Reference lines on the edentulous upper jaw (FIG. 5). The reference symbols in FIG. 5 mean:
      1. incisive papilla (papilla incisiva)
      2. large palate
      3. middle of alveolar ridge
      4. middle of palate
      5. maxillary tuberosity (tuber maxillaris)
      6. Ah line
      7. canine point
   b) Reference lines on the edentulous lower jaw (FIG. 6); maxillary anterior tooth modules
      The reference symbols mean:
      1. retromolar triangle (trigonum retromolare)
      2. middle of alveolar ridge, transversal
      3. middle of alveolar ridge, sagittal
      4. model middle line
      5. stop line
      6. lowest point in the posterior region
3. Maxillary anterior tooth modules
   a) standards for the position of the maxillary anterior teeth
      1. In a normal bite, the central incisors are positioned about 7 mm before the papilla incisiva. The lateral incisors and the canines follow the course of the ridge (FIG. 7).
   b) Standard rules for the orientation of the maxillary anterior teeth
      1. The cutting edge of the central incisors in the upper jaw protrudes beyond the occlusal plane by +/−1 mm.
      2. The cutting edge of the lateral incisors in the upper jaw protrudes beyond the occlusal plane by +/−0.5 mm.
      3. The cutting edges of the incisors run +/− parallel to the occlusal plane.
      4. The tips of the two canines are about on the occlusal plane.
      5. The tips of the two canines have a distance of about 10 mm from the end of the first pair of vestibular folds (FIG. 8).
      6. The connecting line between the two canine tips in the upper jaw (CPC line) runs through the papilla incisiva (FIG. 9).
      7. The labial surfaces of the upper anterior teeth support the upper and lower lips (FIG. 10).

Figure 11:
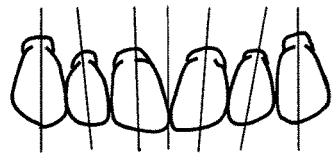
FIG. 11: The Figure shows the axial position of the maxillary anterior teeth from the labial side.

8. Axial position of the maxillary anterior teeth from the labial side.
   #1 vertical
   #2 cervically inclined to the lateral side
   #3 rather vertical, cervically inclined to the vestibular side #1 and #3 are parallel to the bipupillar line in the arch, but according to the positive smile line (FIG. 11). (Lehrbuch der Zahntechnik, Volume 1, A. Hohmann/W. Hielscher, Quintessenzverlag; Die Totalprothese, Gründler/Stüttgen, Verlag Neuer Merkur)

Figure 12:
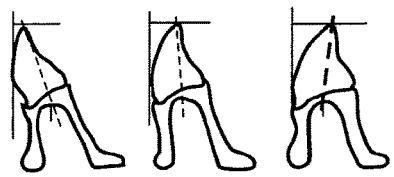
FIG. 12: The Figure shows mandibular anterior tooth modules.
Figure 13:
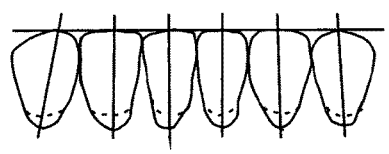
FIG. 13: The Figure shows standard rules for the positions of mandibular anterior teeth.

4. Mandibular anterior tooth modules
   a) Standards for the position of the mandibular anterior teeth all anterior teeth are positioned with the body of the tooth on the center of the alveolar ridge:
      #1 is vestibularly tilted.
      #2 is upright.
      #3 is lingually inclined (FIG. 12).
   b) Standard rules for the orientation of the mandibular anterior teeth
      1. The incisal edges of the lower central incisors correspond exactly to the course of the occlusal plane.
      2. The incisal edges of the lower lateral incisors run +/− parallel to the occlusal plane.
         The tips of the two canines slightly protrude beyond the occlusal plane (FIG. 13). (Lehrbuch der Zahntechnik, Volume 1, A. Hohmann/W. Hielscher, Quintessenzverlag; Die Totalprothese, Gründler/Stüttgen, Verlag Neuer Merkur)

Figure 14:
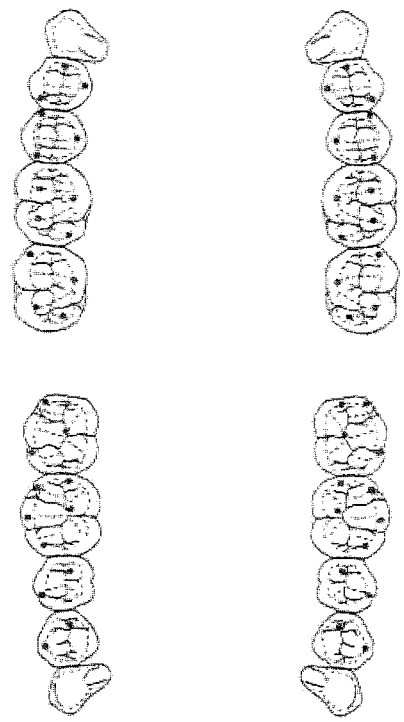
FIG. 14: The Figure shows contact points in the set-up according to conventional methods.

5. Set-up of the posterior teeth according to generally valid criteria
   a) The following applies to the set-up of the mandibular posterior teeth:
      They are usually positioned on the center of the alveolar ridge.
      The central fissures are situated on a straight line running between the tip of the canine and the middle of the retromolar triangle.
      The buccal cusps are situated on the tangent of the Bonwill circle, which reaches from the buccal limit of #4 to the buccal limit of the retromolar triangle.
      The lingual cusp tips are situated on Pound's line.
      They are lingually inclined (=>axial inclination of tooth crown increasing towards the distal).
   b) The following applies to the set-up of the maxillary posterior teeth:
      They are positioned on the center of the alveolar ridge, if possible.
      The central fissures are situated on an elliptical connection line between the tips of the canines and the tubera maxillae.
      Viewed from in front, less and less of the buccal surface CaO be seen from the first premolar to the second molar; this gives rise to the "buccal corridor".
      They are buccally inclined.
      The first lower premolar is set up. The buccal cusp tips touch the occlusal plane.
      The second premolar is set up. It is situated about 1-1.5 mm below the occlusal plane.
      The first lower molar must be set up in the area of the lowest point of the alveolar ridge (chewing center), taking into account the sagittal and transversal compensation curves.
      The buccal cusp tips are about 2 mm below the occlusal plane, rising towards the distal. If there is no danger of proglissement (lower denture forward displacement), the second lower molar CaO also be set up. Otherwise the sagittal progression of the curve in the area of the first molar should be compensated, i.e., distally raised.
      The first upper molar is brought into optimum intercuspation. Subsequently the second upper premolar and then the first upper premolar are inserted into the available space.
      If, as previously described, it was possible to set the second lower molar, the upper antagonists CaO then be added as the last ones, and brought into intercuspation.
   c) In the set-up, the contact points are to be observed according to generally valid criteria (FIG. 14).

Figure 15:
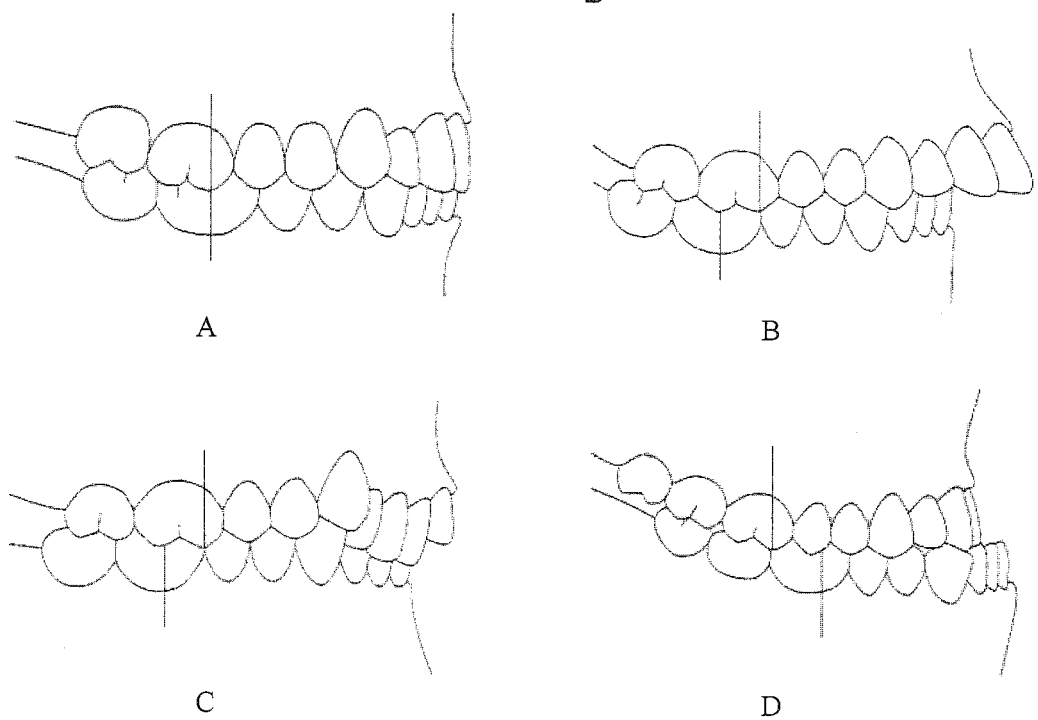
FIG. 15: The Figure shows Angle's bite classifications (Angle classes).

6. Angle's bite classifications (Angle classes as described in Lehrbuch der Zahntechnik, Volume 1, A. Hohmann/W. Hielscher, Quintessenzverlag, pp 130/131)
   Bite classification according to Angle is based on the mesio-distal positional relationship of the first molars. Angle Class I occlusion (normal occlusion or neutral occlusion) (FIG. 15A). The distobuccal cusp of the first lower molar is situated in the central fossa of the first upper molar (purely dental classification).
   a) Class II occlusion (distal occlusion; FIG. 15B)
      The first lower molar is positioned too far distally in relation to the first upper molar (purely dental).
         Class II/1 (syndrome: distal bite). Distal occlusion with protruded upper anteriors, mostly featuring mandibular retrusion with a narrow maxilla, a high palate, a deep bite and an enlarged sagittal overbite.
         Class 11/2 (syndrome: covering bite; FIG. 15C). Distal occlusion with steeply sloping upper anteriors (the lateral incisors often overlap the central incisors from the front side), perspective mostly featuring a retruded mandibular position with a wide, box-shaped maxilla and a deep bite.
   b) Class III occlusion (mesial occlusion; FIG. 15D)
      The first lower molar is positioned too far mesially in relation to the first upper molar (purely dental).
      Class III (syndrome: progenia)
      Mesial occlusion with an inverted anterior overbite (often with protruded upper anteriors and retruded lower anteriors by way of compensation); mostly accompanied by a crossbite in the posterior area, a large chin and a shallow mentolabial fold.

Figure 16:
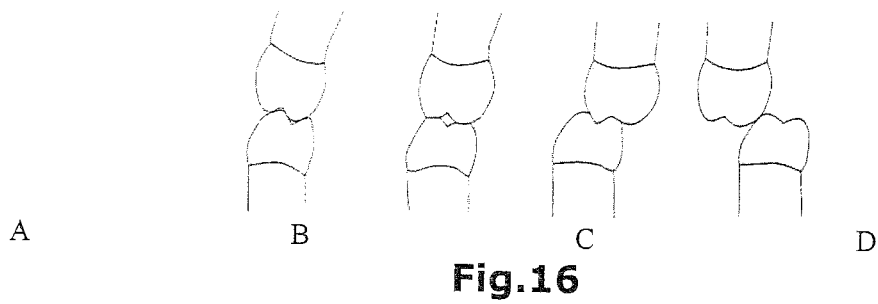
FIG. 16: The Figure shows various bite (occlusion) types.

7. Types of bite
   a) Normal occlusion (FIG. 16A). When the palatal cusps (working cusp) of the maxillary teeth bite into the fossae of the mandibular teeth, this is said to be in normal occlusion.
   b) Edge-to-edge-bite (FIG. 16B). When the cusps of the mandibular teeth bite onto those of the maxillary teeth, this is referred to as an edge-to-edge bite.
   c) Crossbite (FIG. 16C). When the buccal cusps of the lower posteriors protrude vestibularly beyond those of the upper jaw, this is said to be a crossbite.
   d) Scissor bite (FIG. 16D). When the palatal cusps of the upper jaw extend beyond the buccal cusps of the lower jaw vestibularly, this is referred to as a scissor bite.

Library

Figure 17:
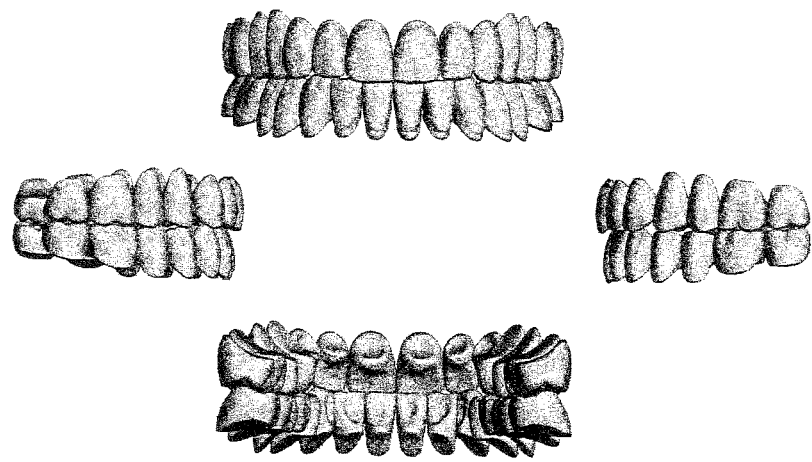
FIG. 17: The Figure shows a tooth library consisting of anterior and posterior teeth.
Figure 18:
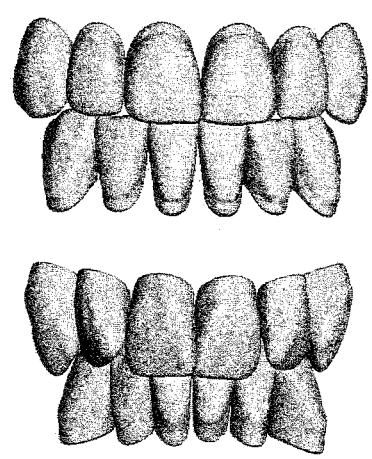
FIG. 18: The Figure shows a number of maxillary and mandibular anterior teeth.
Figure 19:
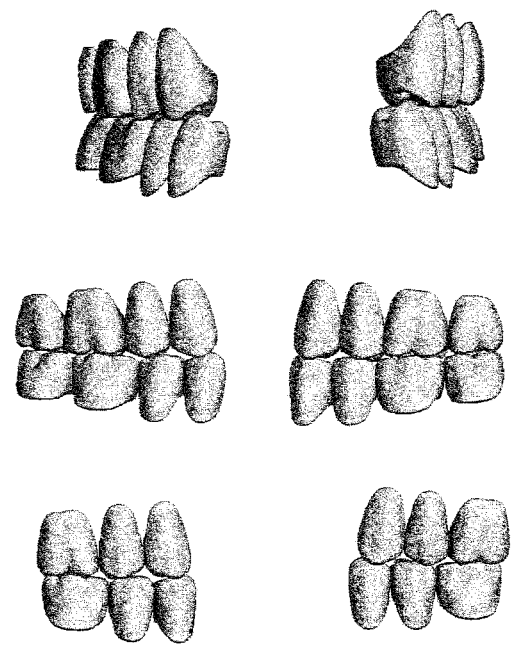
FIG. 19: The Figure shows a number of maxillary and mandibular posterior tooth quadrants.

The library that can be used in the method according to the invention includes a tooth library and a gingival library.
1. Tooth library, especially consisting of anterior and posterior teeth, for example, of the different VITA tooth products in accordance with the VITA mould charts (FIG. 17).

a) A row of #14 maxillary and mandibular teeth together in one block. The set-ups are designed in accordance with the general guidelines and cannot be individualized with respect to the occlusal relationship. For adaptation to slightly larger/smaller dental arches, it is possible to adapt the arches together to be slightly wider/narrower between the maxillary and mandibular incisors. For greater upward/downward deviations, other dental arches from the library that are adapted to the situation are employed.

b) A row of maxillary and mandibular anterior teeth (13 to 23, 33 to 43) which may be arranged separately, in groups or together in one block (FIG. 18). The set-ups are designed in accordance with the general guidelines. For example, the dental arches are positioned with respect to anatomical reference plains such as the occlusal plane line, Camper's plane line, Bonwill's triangle and the like. Anatomical reference points are designed in a virtual model and the position of the dentures is calculated. Advantageously a row of teeth as a block CaO be placed on the jaws instead of an individual placing of the teeth. Here, each individual tooth can be individually varied along the x, y and z axes if necessary (for aesthetic reasons, adaptation to less normal situations). It is also possible to combine the maxillary and mandibular anterior arches individually. A combination with different posterior dental arches is also possible.

c) A row of maxillary and mandibular anterior posterior tooth quadrants (24 to 27/34 to 37; 14 to 17/44 to 47) together in one block (FIG. 19). The set-ups are designed in accordance with the general guidelines. Here, the individual teeth can be moved in the x and y axes only together as a block (upper jaw and lower jaw, the occlusal relationship thus being retained). If needed, the teeth 2/37 and 17/47 can be removed.

2. Gingival Library

Figure 20:
FIG. 20: The Figure shows a gingival library.
Figure 20:
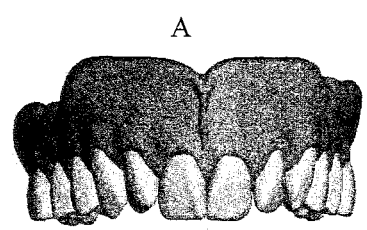
Figure 20:
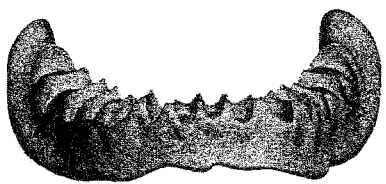
Figure 20:
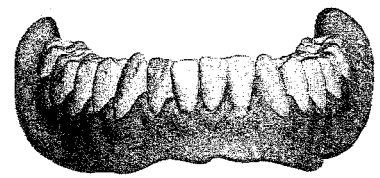

A number of gingival masks (FIG. 20A, D) that, depending on age, offer a variably high course at the teeth, so that the teeth are, depending on the case, more deeply (younger patient) or less deeply (older patient with progressed gum recession) embedded in the gingiva (FIG. 20B, C).

The course along the teeth is connected with the course of the vestibular fold at the virtual model; this yields the outer course of the prosthesis base.

Figure 21:
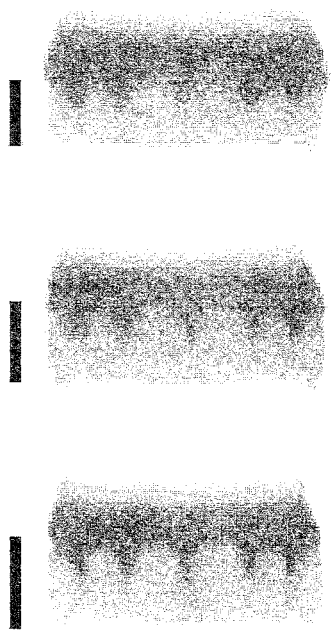
FIG. 21: The Figure shows an example of individually changed dental arch.

Such gingival masks exist for each dental arch. They can also be changed individually (FIG. 21).

The virtually available prosthesis or partial prosthesis as set-up by the method according to the invention can be prepared in reality using the denture base material. Conventional blanks, from which the prosthesis is processed, may also be employed. A particularly suitable blank that can be used according to the invention is an industrially produced denture base material in the shape of a round blank referred to as a milled circle. Conventional denture base materials are offered as single-color preforms, which are polymerized to completion only by the dental technician. Both cold and hot polymerizates are employed. The thus prepared prosthesis bases are subsequently individualized by painting.

An advantage of the denture base materials usable according to the invention is the fact that their multilayered structure already enables them to mimic a natural color gradient, and a corresponding challenge for the artistic ability of the dental technician, which is associated with painting, can be dispensed with.

The basic material of which the novel denture base materials usable according to the invention are made can be based on acrylate chemistry, as with conventional ones. In contrast to the conventional denture base materials, the novel denture base materials usable according to the invention can completely dispense with methyl methacrylate (MMA). However, other polymer materials, such as polyamides, polycarbonates etc., may also be employed.

The novel denture base materials usable according to the invention can contain fillers. In particular, finely dispersed $SiO_2$ or quartz powder can be employed as said filler. The particle size of the filler can typically range from some nm up to about 500 nm. The filler content can be, for example, up to 15% by weight, based on the total weight of the denture base material. In order to achieve some chemical bonding of the filler to the polymer matrix, the filler may be chemically modified, for example, in an upstream process step, for example, by silanization. For this purpose, in particular, a methacrylate-functional silane in a slightly acidic medium can be applied to the $SiO_2$ surface. The methacrylate-functional silanes may also be employed as mixtures of different types in order to obtain specific properties. In particular, 3-methacryloxypropyltrimethoxysilane (MEMO) has proven suitable. For example, the filler can improve the mechanical properties, for example, increase the strength (modulus of elasticity and bending strength).

For coloring, the corresponding pigments can be applied by grinding and mixing by means of a grinding/process, for example, to PMMA beads. Preferably, inorganic color pigments may be employed because of their higher color stability as compared to organic color pigments.

The invention claimed is:

1. A method for preparing a partial or full dental prosthesis comprising:

acquiring measurements of an oral cavity by a digital recording of the oral cavity using an imaging device;

preparing, with a computer, a digital model of the dental prosthesis taking into account the acquired measurements, preparing, with the computer, a virtual gingiva based on the acquired measurements by selecting a matching gingiva design from a digital library containing designs of gingiva, preparing, with the computer, a virtual set-up of teeth based on the acquired measurements by selecting a matching set of teeth from the digital library, the digital library including designs of dental arches, tooth shapes, tooth sizes, and groups of teeth and said library contains total set-ups and/or modular set-ups for Angle's bite classes;

if required, modifying the virtual set-up of teeth with the computer to obtain a fit with the acquired measurements;

virtually embedding the teeth arranged in the virtual set-up in the virtual gingiva; and producing the real prosthesis to correspond to the set-up.

2. The method according to claim 1, wherein said partial or full dental prosthesis is a removable, conditionally removable or permanently attached denture.

3. The method according to claim 1 further comprising individually adapting the dental arch to the individual width of the patient's dental arch by taking virtual hinges into account.

4. The method according to claim 1, wherein the virtual gingiva is based on acquired measurements that include measurements of palatal folds and the Ah line.

5. The method according to claim 1, wherein said producing of the real prosthesis comprises
   a. preparing a prosthesis base;
   b. providing a support for prefabricated teeth receiving means; and
   c. inserting prefabricated teeth into the support, followed by
   d. preparing the total prosthesis.

6. The method according to claim 5, wherein said total prosthesis is prepared by an additive production method.

7. The method according to claim 5, wherein said prosthesis base is prepared by additive production or abrasive production.

8. The method of claim 1 wherein using the imaging device comprises making a camera recording, performing computer tomography, or performing ultrasound.

\* \* \* \* \*

UNITED STATES PATENT AND TRADEMARK OFFICE
CERTIFICATE OF CORRECTION

PATENT NO. : 10,299,898 B2
APPLICATION NO. : 14/407387
DATED : May 28, 2019
INVENTOR(S) : Eva Kerschensteiner and Urban Christen It is certified that error appears in the above-identified patent and that said Letters Patent is hereby corrected as shown below:

On the Title Page

Column 1, Item (73), Line 2, please delete "Sackingan" and insert -- Säckingen --, therefor.

In the Specification

Column 13, Line 43, delete "Hohman/Hielscher." and insert -- Hohmann/Hielscher. --, therefor.

Column 15, Line 54, delete "CaO" and insert -- Can --, therefor.

Column 16, Line 1, delete "CaO" and insert -- Can --, therefor.

Column 16, Line 10, delete "CaO" and insert -- Can --, therefor.

Column 16, Line 32, delete "11/2" and insert -- II/2 --, therefor.

Column 17, Line 21, delete "CaO" and insert -- Can --, therefor.

In the Claims

Column 19, Claim 8, Line 1, delete "of claim 1" and insert -- according to claim 1, --, therefor.

Signed and Sealed this
Thirtieth Day of July, 2019

Andrei Iancu
*Director of the United States Patent and Trademark Office*